United States Patent
Weyl et al.

(10) Patent No.: US 6,849,238 B2
(45) Date of Patent: Feb. 1, 2005

(54) MEASURING SENSOR FOR GASES

(75) Inventors: Helmut Weyl, Schwieberdingen (DE); Hans-Martin Wiedenmann, Stuttgart (DE)

(73) Assignee: Robert Bosch GmbH, Stuttgart (DE)

( * ) Notice: Subject to any disclaimer, the term of this patent is extended or adjusted under 35 U.S.C. 154(b) by 412 days.

(21) Appl. No.: 10/045,743

(22) Filed: Oct. 19, 2001

(65) Prior Publication Data
US 2002/0150507 A1 Oct. 17, 2002

(30) Foreign Application Priority Data
Oct. 20, 2000 (DE) .......................................... 100 52 005

(51) Int. Cl.[7] .................... G01N 31/12; G01N 27/16; G01N 27/00; G01N 9/00; G01N 3/62
(52) U.S. Cl. ............................ 422/94; 422/83; 422/88; 422/95; 422/98; 422/96; 73/1.01; 73/1.02; 73/23.2; 73/23.25; 73/23.26; 73/23.31; 73/23.32; 73/23.4; 73/25.01; 73/35.01
(58) Field of Search .............................. 422/83, 88, 94, 422/95, 98, 96; 73/1.01, 1.02, 23.2, 23.25, 23.26, 23.31, 23.32, 23.4, 25.01, 35.01

(56) References Cited

U.S. PATENT DOCUMENTS

| | | | | |
|---|---|---|---|---|
| 4,155,827 A | * | 5/1979 | Maurer et al. ............... 204/428 |
| 5,880,353 A | * | 3/1999 | Graser et al. ................ 73/23.2 |
| 6,279,376 B1 | * | 8/2001 | Yamada et al. .............. 73/23.2 |
| 6,327,891 B1 | * | 12/2001 | Noda et al. ................ 73/31.05 |
| 6,346,179 B1 | * | 2/2002 | Makino et al. ............. 204/428 |
| 6,360,581 B1 | * | 3/2002 | Murase et al. ............... 73/23.2 |

FOREIGN PATENT DOCUMENTS

| DE | 29 42 494 | 4/1981 |
|---|---|---|
| DE | 30 35 608 | 5/1982 |
| DE | 36 28 572 | 3/1988 |

* cited by examiner

*Primary Examiner*—Jill Warden
*Assistant Examiner*—Brian Sines
(74) *Attorney, Agent, or Firm*—Kenyon & Kenyon

(57) ABSTRACT

The measuring sensor, particularly a lambda probe, has a ceramic sensor member retained at a high temperature during measuring operation. It is shielded from water droplets, carried along in the gas to be analyzed, by a heated protective housing, permeable for the gas to be analyzed, by which water droplets carried along in the direction of the sensor member are evaporated before reaching the sensor member. In this way, the water droplets are unable to cause any shock-like temperature drops at spots on the surface of the sensor member or material flaking.

18 Claims, 1 Drawing Sheet

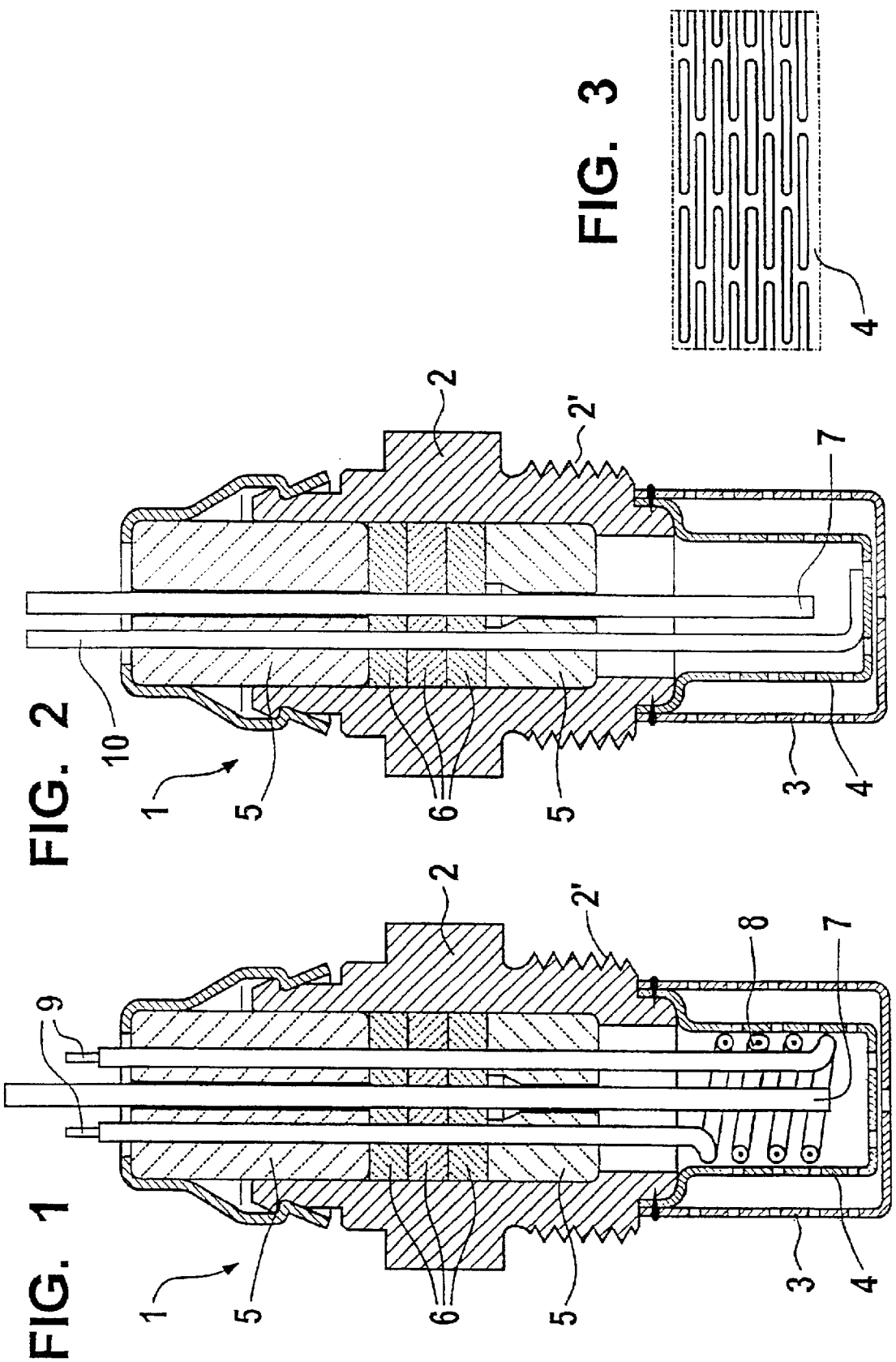

MEASURING SENSOR FOR GASES

FIELD OF THE INVENTION

The present invention relates to measuring sensors for gases, particularly lambda probes, for determining the oxygen content of a gas to be analyzed, having a ceramic sensor member which is arranged in a protective housing permeable to the gas to be analyzed and which, during measuring operation, is heated by its own heating to a high temperature, e.g. 300° C. to 450° C., and retained at this temperature.

BACKGROUND OF THE INVENTION

Exhaust systems of modern internal combustion engines, particularly in the case of motor vehicles, are regularly provided today with catalytic converters for the catalytic decomposition of harmful exhaust gases. In order for the catalytic converters to function well, it is necessary to feed air and fuel to the engine in a predefined proportion. The engine controls provided for this purpose are connected on their input side to a so-called lambda probe whose signals represent the composition of the exhaust gas and thus enable the engine control to adjust the ratio of fuel and combustion air in a manner optimal for the catalytic converter.

In the case of the measuring sensors indicated at the outset, the ceramic sensor member is constructed at least region-wise as a solid electrolyte member which is conductive for oxygen ions. This conductivity is utilized to generate an electrical signal correlated to the oxygen concentration of the gas to be analyzed.

Since the effect of the conductivity for oxygen ions is strongly temperature-dependent, the sensor member must be heated during measuring operation in order to be able to generate evaluable signals. Typical operating temperatures of the sensor member lie between 300° C. and 450° C.

German Patent No. 30 35 608 describes a measuring sensor of the type indicated at the outset. In that case, the sensor member is constructed as a ceramic solid electrolyte tube which has heating arranged on the outside wall and is preferably accommodated in a protective sleeve having openings for the entrance of the gas to be measured.

German Patent No. 29 42 494 likewise describes a measuring sensor whose sensor member is constructed as a ceramic solid electrolyte tube. The heating is arranged on the inner side of a protective housing which accommodates the sensor member and is provided with an opening for the gases to be analyzed. Thus, the housing forms a heating and protective sleeve for the sensor member which is heated indirectly in this configuration.

German Patent No. 36 28 572 describes a tubular ceramic sensor member which is made of electrically conductive ceramic material on its measuring-gas-side end, and the remainder of which is made of electrically insulating ceramic material, the region of electrically insulating ceramic material bearing electrical heating conductors on the exterior.

SUMMARY OF THE INVENTION

According to the present invention, working with the measuring sensor indicated at the outset, a protective housing or protective sleeve with a double casing is provided whose inner casing is heated.

This offers the advantage that water droplets, possibly carried along in the gas to be analyzed, will evaporate with high probability before they can strike the sensor member. Accordingly, water droplets are prevented from causing shock-like spot temperature drops with extreme temperature gradients on the sensor member that can lead to flaking off of material.

To make the measuring sensor ready for operation quickly after a motor vehicle is started, the heating of the sensor member is designed so that it already reaches a temperature of over 300° C. after a few seconds. On the other hand, the exhaust branch of a motor vehicle warms up only quite slowly, particularly at low ambient temperatures, with the result that the exhaust-gas temperatures can remain below the dew point for water for a longer time and the measuring sensor is "bombarded" with water droplets accordingly. According to the present invention, virtually only water vapor, which is not critical with respect to the service life and performance reliability of the sensor member, acts upon the sensor member.

According to one preferred specific embodiment of the present invention, the additional heating in the vicinity of the sensor member produces a temperature gradient with a temperature rising toward the surface of the sensor member. A particularly effective vaporization of the water droplets is thereby achieved.

In particular, this temperature gradient can be implemented in that the protective housing has an unheated outer casing, as well as a heated inner casing, separated therefrom by a clearance space, whose temperature on the one hand is markedly lower than the surface temperature of the sensor member, and on the other hand is higher than the temperature of the outer casing and preferably lies near to or barely above the evaporation temperature of water.

Incidentally, the desired vaporization of the water droplets can even be improved in that the protective housing, and particularly its inner casing, have surfaces easily wetted by water.

The double casing of the protective housing offers the further advantage that the outer casing can reduce the droplet stream to the sensor member, and thus facilitate the vaporization work of the heated inner casing.

BRIEF DESCRIPTION OF THE DRAWINGS

FIG. 1 shows a sectional view of a first advantageous specific embodiment.

FIG. 2 shows a corresponding sectional view of a modified specific embodiment.

FIG. 3 shows a top view of the rolled-out inner side of the inner casing of a double-casing protective housing of the sensor member.

DETAILED DESCRIPTION

Measuring sensor 1 shown in FIG. 1 has, as an outer holding device, a collet 2 which, with an external thread 2', can be screwed into place in a corresponding threaded opening of a motor-vehicle exhaust branch (not shown). At its end, which is the lower end in the drawing and which extends into the exhaust branch, collet 2 bears an outer protective sleeve 3, as well as an inner protective sleeve 4 that is set apart from the inner side of outer protective sleeve 3. Both protective sleeves 3 and 4 are provided with perforations permitting a gas exchange between the interior of inner protective sleeve 4 and the exterior surroundings of outer protective sleeve 3. Both collet 2 and protective sleeves 3 and 4 can be constructed as metal parts; protective sleeves 3 and 4 can be welded to collet 2, or can be joined by a pinned fitting or in another manner.

Arranged within collet 2 are ceramic filling bodies 5 and sealing packings 6 which support a ceramic gas sensor element 7 that, with its lower end in the drawing, extends into the interior of inner protective sleeve 4. This end of gas sensor element 7 is brought to a very high temperature, e.g. 300° C. to 450° C., by a heater (heating) (not shown) embedded in the ceramic sensor member. The electrical connections of this heating, as well as the connections of electrodes (not shown) of gas sensor element 7, are placed at the upper end of gas sensor element 7 in the drawing.

In addition, filling bodies 5 and sealing packings 6 support a heater coil 8, positioned within inner protective sleeve 4, whose electrical resistance wire used for generating heat is arranged in an enclosing tube that is electrically insulated with respect to the resistance wire and which, with two end regions, penetrates filling bodies 5 and sealing packings 6 and bears heating-wire connections 9.

Thus, due to the arrangement of the electrical resistance wire, used for generating heat, in the enclosing tube which is insulated with respect to this wire, no electrical potential whatsoever can appear between the resistance wire used for generating heat, and filling body 5 and sealing packings 6, respectively, or sensor element 7.

During operation of measuring sensor 1, heater coil 8 is heated in such a way that a temperature in the vicinity of the evaporation temperature of water, preferably a temperature between 80° C. and 150° C. is reached and maintained on the coil surface and on the surface of inner protective sleeve 4, respectively. In this context, heater coil 8 is designed such that, after the start of measuring operation, the aforesaid temperatures are reached at least within the same time span of 10 seconds at a maximum, within which gas sensor element 7 is brought by its heating to the operating temperature of approximately 300° C. to 450° C.

All these temperatures indicated above are also reached within the aforesaid time span when the surroundings of the measuring sensor, particularly a motor-vehicle exhaust branch (not shown) accommodating the measuring sensor, is completely chilled through because of very low ambient temperatures, so that the temperature in the exhaust branch remains below the dew point of water for a longer time, and therefore it must be expected that the exhaust gases will carry along water droplets.

It may be that these water droplets act upon measuring sensor 1, however cannot reach gas sensor element 7:

Outer protective sleeve 3, which is unheated and accordingly remains at a similar low temperature as the exhaust branch, acts, because of the perforations formed in it which are made of a plurality of holes having very narrow cross-sections, like a type of flow restrictor for the striking water droplets. This is essentially synonymous with the fact that the water droplets are only able to enter through the perforations into the interior of outer protective sleeve 3 in a retarded manner and in reduced quantity.

There, they strike with the highest probability on inner protective sleeve 4, upon which they quickly evaporate, since the temperature of inner protective sleeve 4 is close to the evaporation temperature of water. Water droplets nevertheless still passing through the narrow perforations of inner protective sleeve 4 have only a reduced droplet mass because of the previous partial evaporation, and moreover, because of the heat radiation of the inner protective sleeve, have a temperature close to the evaporation temperature of water. These already heated residual droplets are finally evaporated on the remaining path to sensor element 7 before they can strike upon very hot sensor element 7.

The aforesaid evaporation process of the water droplets is promoted in that, on the way from outer protective sleeve 3 to sensor element 7, the droplets pass through a region with a temperature gradient rising toward sensor element 7, so that the water droplets can be heated with a high efficiency factor and finally evaporated.

Thus, as a result, only water vapor is able to act upon very hot sensor member 7. The performance reliability and service life of sensor element 7 can in no way be impaired by this. This is probably based essentially on the fact that the vapor density in the region of sensor element 7 has virtually the same value on the entire surface of sensor element 7, and accordingly, identical surface temperatures exist everywhere on sensor element 7, as well.

However, avoided in each case is that, due to water droplets striking on sensor element 7, shock-like temperature drops can occur at spots on the surface of sensor element 7 and, as a result of these temperature drops, material flaking can also occur.

The exemplary embodiment in FIG. 2 differs from the exemplary embodiment described above essentially in that inner protective sleeve 4 is constructed as an electrical resistance heater, the electrical heating circuit taking a course via a connecting wire 10 which penetrates filling members 5 and sealing packings 6, is preferably electrically insulated with respect to filling member 5 and sealing packings 6 and is electroconductively connected to inner protective sleeve 4, as well as via inner protective sleeve 4 and metal collet 2 electroconductively connected to it; the collet, on its part, being electrically connected to parts which are switched as an electrical ground line and are electrically connected to one pole of an electrical current source, respectively.

FIG. 3 shows a plan view of a rolled-out segment of the circumference of inner protective sleeve 4 according to one preferred specific embodiment. It can be seen that the circumferential wall has a net-like structure with slot-shaped perforations extended in the circumferential direction.

Because of this filigree structure, inner protective sleeve 4 is suitable on one hand as a heating element of an electrical resistance heater. On the other hand, good wettability with water droplets is achieved, with the result that the water droplets stick with increased probability to protective sleeve 4 and disperse over a large surface, so that they can be easily and effectively evaporated because of the heating of inner protective sleeve 4.

In principle, outer protective sleeve 3 can be constructed in the same manner as inner protective sleeve 4. Optionally, it is expedient to construct outer protective sleeve 3 with increased mechanical stability.

If desired, protective sleeves 3 and 4 may also be made of a porous or foam-like structured metal or a porous or foam-like ceramic.

In all the specific embodiments described, the heating provided for evaporating the water droplets can be switched off as soon as the ambient temperature, i.e. the temperature of an exhaust branch of an internal combustion engine, has risen sufficiently and condensation of water need no longer be expected.

What is claimed is:

1. A measuring sensor for determining an oxygen content of a gas to be analyzed, comprising:
   a protective housing permeable for the gas to be analyzed, the protective housing including a double casing, the double casing including an inner casing;
   a first heater configured to heat the inner casing; and a ceramic sensor member situated in the protective housing, the ceramic sensor member including a second heater configured to heat, during a measuring operation, the ceramic sensor member to a temperature above 300° C. and to retain the ceramic sensor member at a temperature above 300° C.

2. The measuring sensor according to claim 1, wherein the first heater is configured to produce a temperature gradient with a temperature rising toward a surface of the sensor element.

3. The measuring sensor according to claim 1, wherein the first heater is configured to heat the inner casing to a surface temperature above an evaporation temperature of water.

4. The measuring sensor according to claim 1, wherein the first heater is configured to heat the inner casing to a surface temperature below an evaporation temperature of water.

5. The measuring sensor according to claim 1, wherein the protective housing includes an unheated outer casing, and the heated inner casing is separated from the outer casing by a clearance space.

6. The measuring sensor according to claim 1, wherein the first heater is arranged in a self-supporting manner on an inner side of the inner casing.

7. The measuring sensor according to claim 1, wherein the inner casing is constructed as a heating element.

8. The measuring sensor according to claim 1, wherein at least an outer side of the inner casing is configured to be easily wetted by water.

9. The measuring sensor according to claim 8, wherein the protective housing includes an outer casing, the outer casing also configured to be easily wetted by water.

10. The measuring sensor according to claim 1, wherein the first heater is configured to heat the inner casing to a temperature between 80° C. and 150° C. and to retain the inner casing at a temperature between 80° C. and 150° C.

11. The measuring sensor according to claim 1, wherein the measuring sensor is configured as a lambda probe.

12. The measuring sensor according to claim 1, wherein the first heater is configured to produce a temperature gradient with a temperature rising toward the a surface of the ceramic sensor member and to provide for vaporization of water.

13. The measuring sensor according to claim 1, wherein the protective housing includes perforations.

14. The measuring sensor according to claim 7, wherein the heating element includes an electrical resistance heater.

15. The measuring sensor according to claim 1, wherein the protective housing includes one of a metal, a porous metal, and a porous ceramic.

16. The measuring sensor according to claim 1, wherein at least one of the first heater and the second heater is configured to be switched off when an ambient temperature has risen and condensation of water is not expected.

17. The measuring sensor according to claim 16, wherein the ambient temperature includes a temperature of an exhaust branch of an internal combustion engine.

18. The measuring sensor according to claim 1, wherein the heater coil includes an electrical resistance wire.

* * * * *